United States Patent [19]
Beers

[11] Patent Number: 6,051,185
[45] Date of Patent: Apr. 18, 2000

[54] APPARATUS FOR PERFORMING GAMMA IRRADIATION

[75] Inventor: Eric Beers, Alameda, Calif.

[73] Assignee: SteriGenics International, Fremont, Calif.

[21] Appl. No.: 08/767,351

[22] Filed: Dec. 18, 1996

[51] Int. Cl.[7] .................................. A61L 2/08; G21K 5/10
[52] U.S. Cl. ...................... 422/22; 422/186; 250/453.11; 250/454.11; 250/455.11
[58] Field of Search ................ 422/22, 186; 250/453.11, 250/454.11, 455.11, 515.1, 517.1

[56] References Cited

U.S. PATENT DOCUMENTS

| | | | |
|---|---|---|---|
| 1,780,108 | 10/1930 | Barry | 250/517.1 |
| 2,932,745 | 4/1960 | Alberti et al. | 250/517.1 |
| 2,942,115 | 6/1960 | O'Connell | 250/517.1 |
| 3,092,218 | 6/1963 | Clay | 250/517.1 |
| 3,334,597 | 8/1967 | Ruskin et al. | 250/517.1 |
| 3,614,446 | 10/1971 | Leuthold et al. | 250/517.1 |
| 3,680,498 | 8/1972 | Roos | 250/517.1 |
| 3,995,165 | 11/1976 | Buth et al. | 250/517.1 |
| 4,074,141 | 2/1978 | Bryant | 250/517.1 |
| 4,153,845 | 5/1979 | Fava | 250/517.1 |
| 4,514,640 | 4/1985 | Bagnell et al. | 250/517.1 |
| 4,608,495 | 8/1986 | Jacobson | 250/517.1 |
| 4,638,166 | 1/1987 | Baudro | 250/517.1 |
| 4,760,264 | 7/1988 | Barrett | 250/453.11 |
| 4,788,701 | 11/1988 | Barrett | 250/453.11 |
| 5,008,550 | 4/1991 | Barrett | 250/453.11 |
| 5,400,382 | 3/1995 | Welt et al. | 250/454.11 |
| 5,633,508 | 5/1997 | Schleppenbach | 250/517.1 |
| 5,763,735 | 6/1998 | Stahl et al. | 250/517.1 |

FOREIGN PATENT DOCUMENTS

| | | |
|---|---|---|
| 2360016 | 6/1975 | Germany . |
| 61-204592 | 9/1986 | Japan . |
| 07310481 | 11/1995 | Japan . |
| 2040644 | 10/1993 | Spain . |

*Primary Examiner*—Elizabeth McKane
*Assistant Examiner*—Fariborz Moazzam
*Attorney, Agent, or Firm*—McCutchen, Doyle, Brown & Enersen

[57] ABSTRACT

Apparatuses and methods are disclosed for irradiating products. The apparatuses and methods can be used to sterilize or reduce the microbiological contamination in materials introduced into the apparatus. The apparatus includes a biological shield made from modules. It also includes a batch operated material handling system capable of moving product into a cell area without requiring an operator to enter the cell area. The apparatus is of a size that can be constructed in existing buildings. It can be decommissioned and moved to different locations. The methods disclosed include moving products into a cell area without an operator entering the cell area and subjecting the products to radiation.

19 Claims, 10 Drawing Sheets

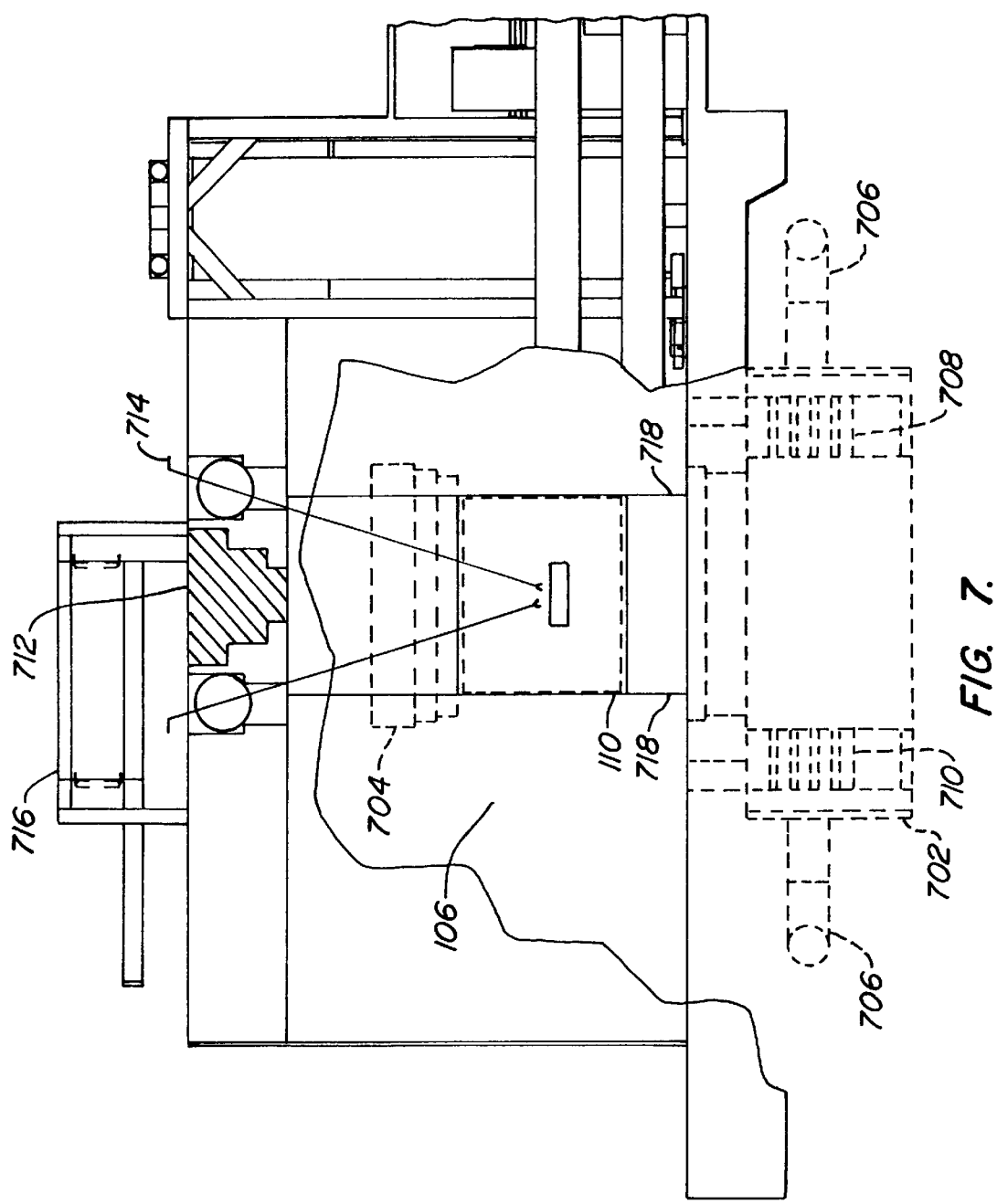

APPARATUS FOR PERFORMING GAMMA IRRADIATION

BACKGROUND

Gamma irradiators are used to deliver a pre-determined amount of gamma radiation in a controlled manner to products. Controlled amounts of gamma radiation are used to sterilize products, such as single use syringes, surgical gloves, laboratory ware and other disposable medical devices. Products such as food packaging, spices and other foods are treated with lower levels of radiation to reduce microbiological contamination. Irradiators provide a mechanism to irradiate products while closely regulating the amount of radiation to which products are exposed and confining the radiation to a limited area.

Gamma irradiators commonly have a cell area in which the products are treated with radiation. Various types of walls, shields, and mazes are used to prevent radiation from leaving the cell area. The products are introduced into the cell area either manually in a batch system or on a conveyor in a continuous loading system, the radiation source is mechanically moved from its storage position into the operating position for irradiation. During processing, radiation from the raised source effectively kills organisms anywhere in or on the products which pass through the irradiator. The absorbed dose delivered to the products is a function of the time the product is exposed to the radiation source, the quantity of cobalt-60 isotope or other radiation source in the system, the distance the product is from the radiation source and the density of the product itself.

The walls, shield, maze or other structure surrounding the cell area dictates the design of the irradiator. The structure surrounding the cell area must absorb the gamma radiation after it passes through the product being irradiated to ensure that the outside of the shield maintains radiation levels required by the United States Nuclear Regulatory Commission ("USNRC") and the International Atomic Energy Agency ("IAEA") regulations (currently less than 2 millirem per hour).

Irradiators of an industrial scale, now known to the industry, use a "poured in place" steel reinforced concrete design for the structure. In order to comply with the required radiation levels outside of the cell area, these irradiators generally have wall thicknesses in excess of six feet to adequately shield radiation source capacities from 3 to 12 Megacuries. The typical size of the shielding structure of a large industrial irradiator system is from 2000 to 4000 square feet. Irradiators of this size built using poured in place concrete construction are impractical to build in existing buildings because of their large size and the requirements of standard construction techniques. In addition, irradiators constructed of standard poured in place concrete cannot be fully decommissioned and moved to other locations. In addition, all construction must take place on-site adding to the cost and construction time of the facility.

Large irradiators also have disadvantages in operation. They cannot effectively and economically process a small volume of product in geographic locations. Because standard irradiators are large and immovable, they can be built only in limited locations where volumes are large enough to justify the facility. When irradiating small quantities of product, it is not economically feasible to transport the products long distances to the location of the irradiator. In addition, the large size of the cell area of standard irradiators makes processing of small amounts of product inefficient.

The shielding structure in an industrial sized irradiator commonly includes some kind of maze design to allow access to the cell area. The product enters the cell area through the maze where the many turns in the maze prevent radiation from leaving the cell area. This maze design further increases both the size and cost of the shielding structure.

Irradiators also include a system for transporting the products into and out of the cell area and around the radiation source. This system can be a system of conveyors, which continually cycles product into and out of the cell area, or a batch system. Existing batch style irradiators of an industrial size require the operators to physically enter the cell area through the maze between batch runs to exchange the processed product for the new batch of product to be processed. Any requirement that personnel enter into the cell area inherently decreases the safety of the irradiator.

Irradiators also commonly include a source system which stores the radiation source when the irradiator is not processing product and moves the source into position for processing. The source system in standard radiators includes a rectangular pool of water below the floor of the cell area to store the source when it is not in use. The depth required to adequately shield the radiation source can make construction of the storage system impractical or prohibitively expensive in certain locations due to soil conditions or other environmental factors. In addition, the excavation required for the rectangular shape of the pool can be expensive to construct.

For the foregoing reasons, there is a need for a movable and moderately sized gamma irradiator that operates efficiently and economically.

SUMMARY

The present invention encompasses apparatuses and methods for subjecting materials to controlled amounts of gamma radiation which overcome the above mentioned disadvantages of prior irradiators and methods. An apparatus according to the present invention can be used to sterilize or reduce the microbiological contamination in materials introduced into the apparatus.

An irradiator according to the present invention is more compact than irradiators currently in use. It can be disassembled and moved. In addition, products can be transported into the irradiator with minimal operator exposure. The wall construction of the irradiator allows modular construction of the irradiator. The modules that form the walls of the irradiator can be made of steel or preformed concrete panels. A preferred embodiment of the present invention includes an integrated shielding door, which makes possible a batch type material handling system which does not require the operator to enter the biological shield between batches.

The many advantages of the present invention will become clear to those skilled in the art from the present disclosure. Among many other advantages, the present invention offers the following advantages over existing apparatuses:

The present invention allows an irradiator to be assembled in modules inside an existing building without the disruption of full concrete poured construction.

The present invention is less expensive than existing technologies.

The present invention is safer to operate than existing batch irradiators.

The present invention is more versatile than existing technologies.

The present invention is capable of processing a small volume of material more efficiently and economically than existing technologies.

In the present invention, no entry to the cell area is required between processing batches, which improves both the physical speed of product interchange and the inherent safety of the system by reducing the number of cell entries to a minimum.

The present invention is capable of processing materials at a faster rate than existing batch irradiators.

The present invention can be decommissioned and later reassembled in a different location.

Among other advantages, the present invention offers advantages over conventional irradiator systems because it integrates a biological shield constructed in removable modules which includes a full shielding door with a batch material handling system which eliminates the need for the operator to enter the cell area between batches, source storage options, and a control and monitoring system.

These and other features and advantages of the present invention will become better understood with regard to the following drawings, detailed description, and claims.

BRIEF DESCRIPTION OF THE DRAWINGS

FIG. 7 shows a cut away elevation of the dry type source system in an embodiment of the present invention.

DETAILED DESCRIPTION OF PREFERRED EMBODIMENTS

A preferred embodiment of the invention combines a unique biological shield design, including an integrated shielding door design, with an efficient radiation source system, a batch operated material handling system, and a control and monitoring system to create a gamma irradiator which is lower in cost to build, more flexible for processing and offers more options for placement and decommissioning than irradiators currently in use. An embodiment of the invention is shown in FIGS. 1–7.

Figure 1:
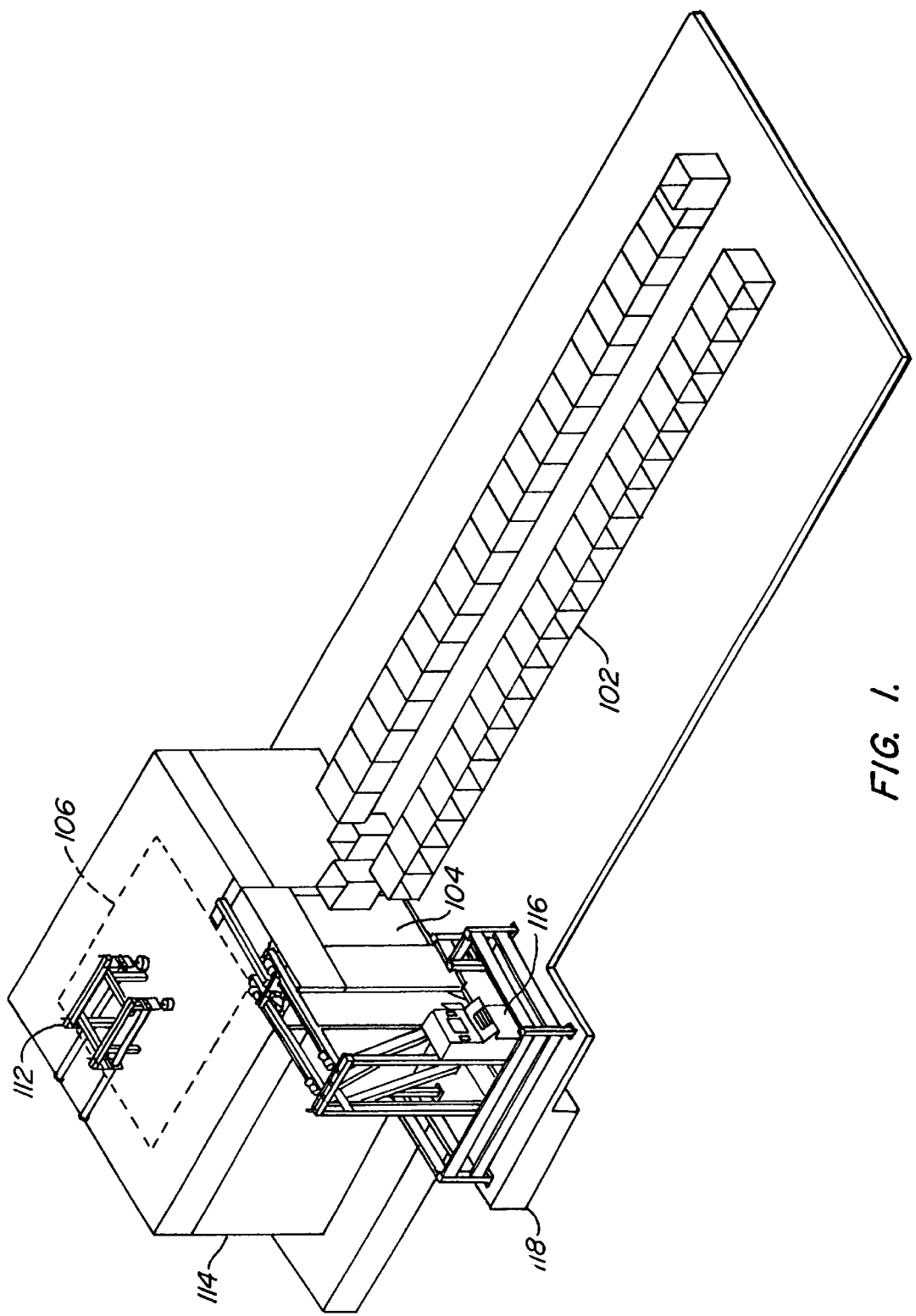
FIG. 1 shows an embodiment of the present invention.

FIG. 1 shows a preferred embodiment of the invention. The main structure of the irradiator of the preferred embodiment surrounds the cell area 106, the area in which products are subjected to the radiation. The cell area is surrounded by the biological shield 114 which prevents radiation from escaping the cell area 106. In the biological shield 114 is a shielding door 104. The biological shield 114 is assembled on a poured concrete foundation 118. The embodiment includes a material handling system 102 which transports the product to be irradiated through the shielding door 104 and into the cell area 106. The embodiment also includes a source system 112 for storing the radiation source when the irradiator is not in processing mode and lifting the radiation source into the cell area 106. The source system 112 may be either a dry or wet source system. The radiation source itself is assembled in the source racks 110 (shown in FIGS. 6 and 7) which are a part of the source system 112. All operations of the irradiator are controlled by the control and monitoring system 116.

Biological Shield

Figure 2A:
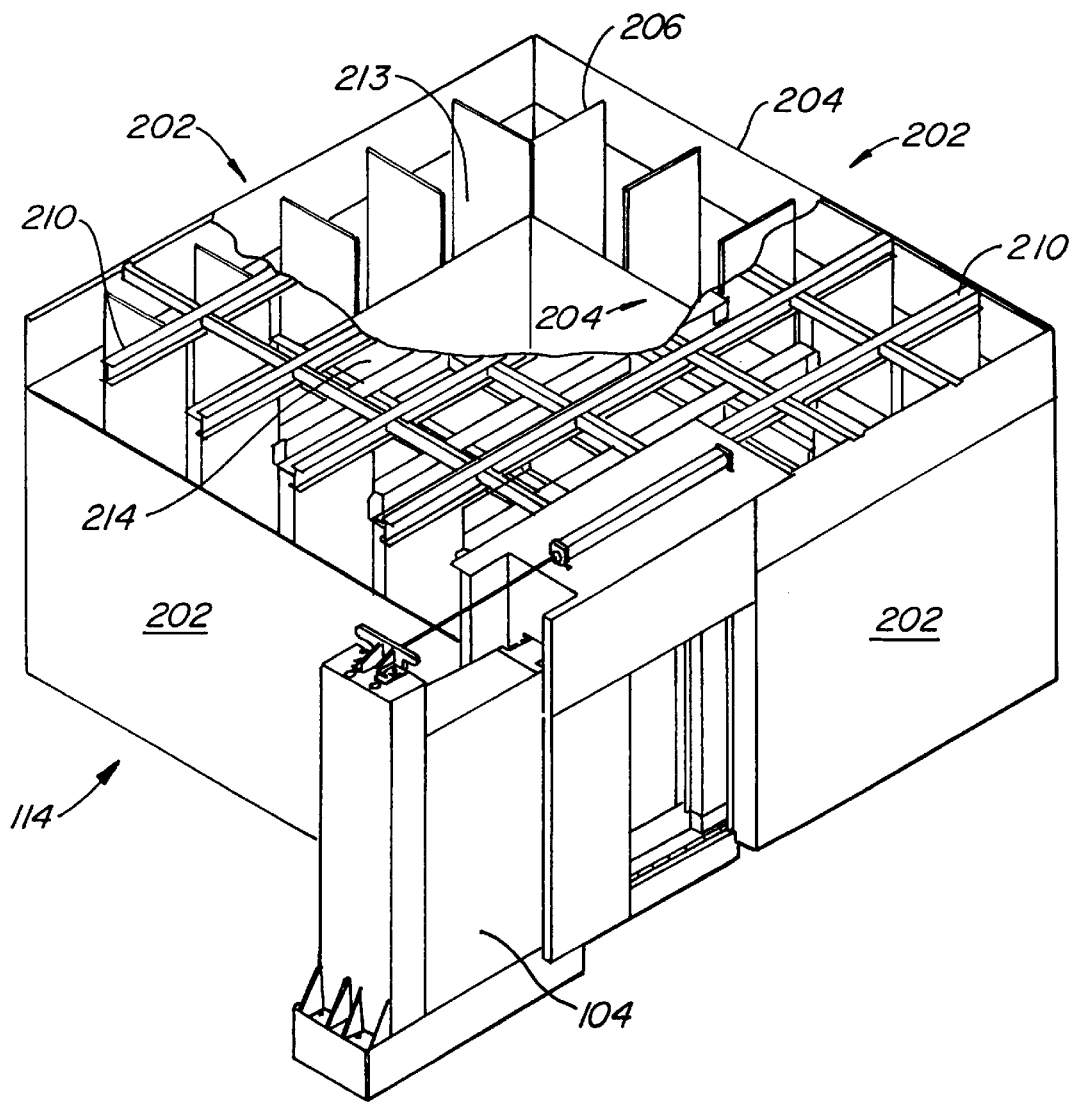
FIG. 2a shows the walls and roof of the steel biological shield in an embodiment of the present invention.
Figure 2B:
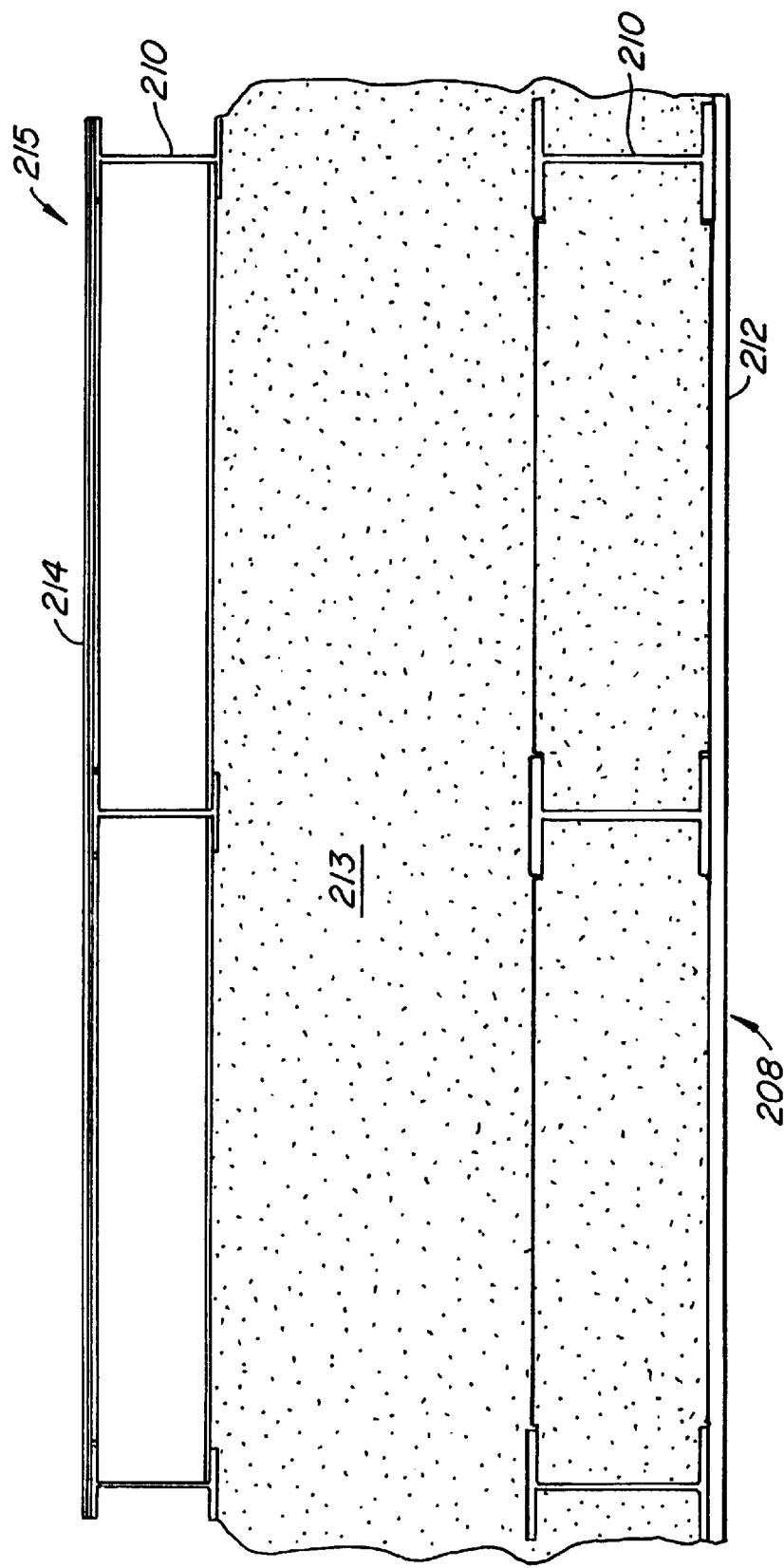
FIG. 2b shows a cross section of the roof of the steel biological shield in an embodiment of the present invention.

FIG. 2a shows the biological shield 114 in a preferred embodiment of the invention. The construction design of the walls of the biological shield 114 features pre-cut steel modules 202 which form a shell. The four modules 202 may be prefabricated at an off-site manufacturer and shipped to the building site for erection and final assembly. The four modules 202 make up the four walls of the rectangular structure. The modules 202 are constructed of one inch thick mild steel plates 204. The steel plates 204 are welded to stiffeners 206 placed at 90 degrees to the steel plates 204. These stiffeners 206 also are fabricated from one inch steel plate. A roof of steel I beams 210 and steel plate 214 is positioned on top of the walls of the biological shield 114 as shown in FIG. 2a. A cross section of the roof of the biological shield 114 is shown in FIG. 2b.

The inside roof 208 of the biological shield 114 is constructed of a grid of steel I beams 210 and a one-inch thick steel plate 212. The I beams 210 are positioned on the same centers as the wall stiffeners 206 shown in FIG. 2a and are used to span the roof area to provide support. The steel plate 212 is welded to the bottom of the I beams 210 and serves as the ceiling for the cell area 106. The upper roof 215 also is constructed of a grid of steel I beams 210. One-quarter inch thick steel panels 214, which can be removed to inspect the level of ballast in any area of the system during regular maintenance, are placed in the areas between the I beams 210 in the upper roof 215.

The void created by the steel plate structure forming the walls and roof of the biological shield 114 is filled with a steel ballast material 213 with a minimum in place density of 270 pounds per cubic foot. The steel ballast material 213 is poured into the void after final assembly of the steel modules. The ballast pour will be continuous up through the full height of the walls and roof of the biological shield 114 to ensure no gaps arise from the pour. Based on the steel ballast density and using a shielding calculation program called Microshield 4©, preferably the wall fill thicknesses of the biological shield 114 are at least 36 inches for the walls 90 degrees to the source racks 110 and 38 inches for the walls parallel to the source racks 110. Preferably, the thickness of the ballast material 213 in the roof is a minimum of 36 inches, which includes four inches of material to allow for possible ballast settling over time.

Preferably, the inside height of the biological shield 114 is 8.5 feet which is defined by the minimum vertical clearance required for the mechanisms in the cell area 106. Preferably, the outside height of the biological shield 114 is 12.02 feet which is defined by the thickness of shielding required to maintain radiation levels below two millirem per hour outside of the biological shield 114 as defined by the USNRC and the IAEA regulations and the structure to support it.

The cell area 106 is the area inside the biological shield 114. Preferably, the cell area is 14 feet wide when measured perpendicular to the source racks 110 and 15 feet wide when measured parallel to the source racks 110. This design will allow for the modules 202 to be assembled on a poured concrete foundation 118 inside an existing building without the disruption of a full concrete poured construction. The poured concrete foundation 118 should be appropriate for local soil conditions. Preferably, the foundation includes a five (5) inch deep trench into which the modules 202 of the biological shield 114 can be inserted.

Figure 2C:
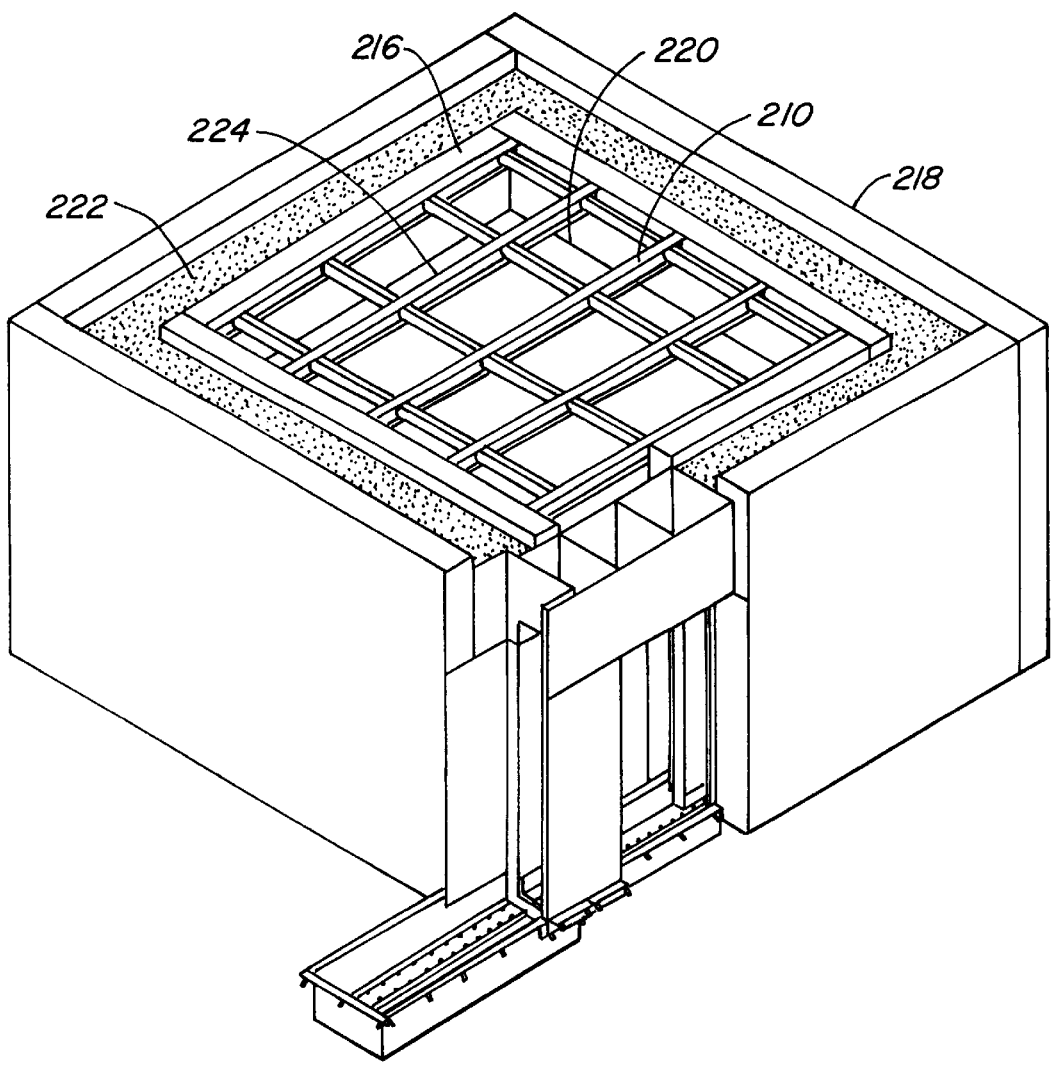
FIG. 2c shows the modular concrete biological shield in an embodiment of the present invention.

FIG. 2c shows the biological shield 114 in an alternative embodiment of the present invention. In this alternative construction, the inner steel plate walls are replaced with 18 inch thick reinforced inner concrete panels 216 and the outer steel plate walls are replaced with 12 inch thick reinforced outer concrete panels 218. The inner roof 220 is constructed of an 18 inch reinforced concrete panel, supported on the inner concrete panels 216. The upper roof 224 will be of the same design as in the steel biological shield 114 illustrated in FIG. 2b and is supported by the inner concrete panels 216. The concrete panels can be either purchased as pre-cast or formed and poured at the site depending on the local availability of materials. The steel ballast fill 222 required is of the same type as the steel panel construction. However, the width of the ballast fill between the walls could be reduced to 25 inches for the walls 90 degrees to the source racks 110 and 27 inches for the walls parallel to the source racks 110. The overall external size of the biological shield 114 will be approximately eight inches greater in each direction than the size of a similar biological shield 114 constructed of steel plates.

The concrete design may be more cost or time effective to build in remote areas where either shipping of steel material is costly or the availability of adequate steel welding and handling skills is not adequate for the specific job of assembly. For example, in some areas the logistics or economics of shipping steel plate modules to the site may be impractical.

One skilled in the art will recognize from this disclosure that different steel plate, stiffener, and concrete panel thicknesses with corresponding changes in the amount of steel ballast to achieve adequate shielding may be used in the present invention. Both the steel and concrete shield constructions should be seismically designed to meet the appropriate codes for international installation.

Shielding Door

Figure 3A:
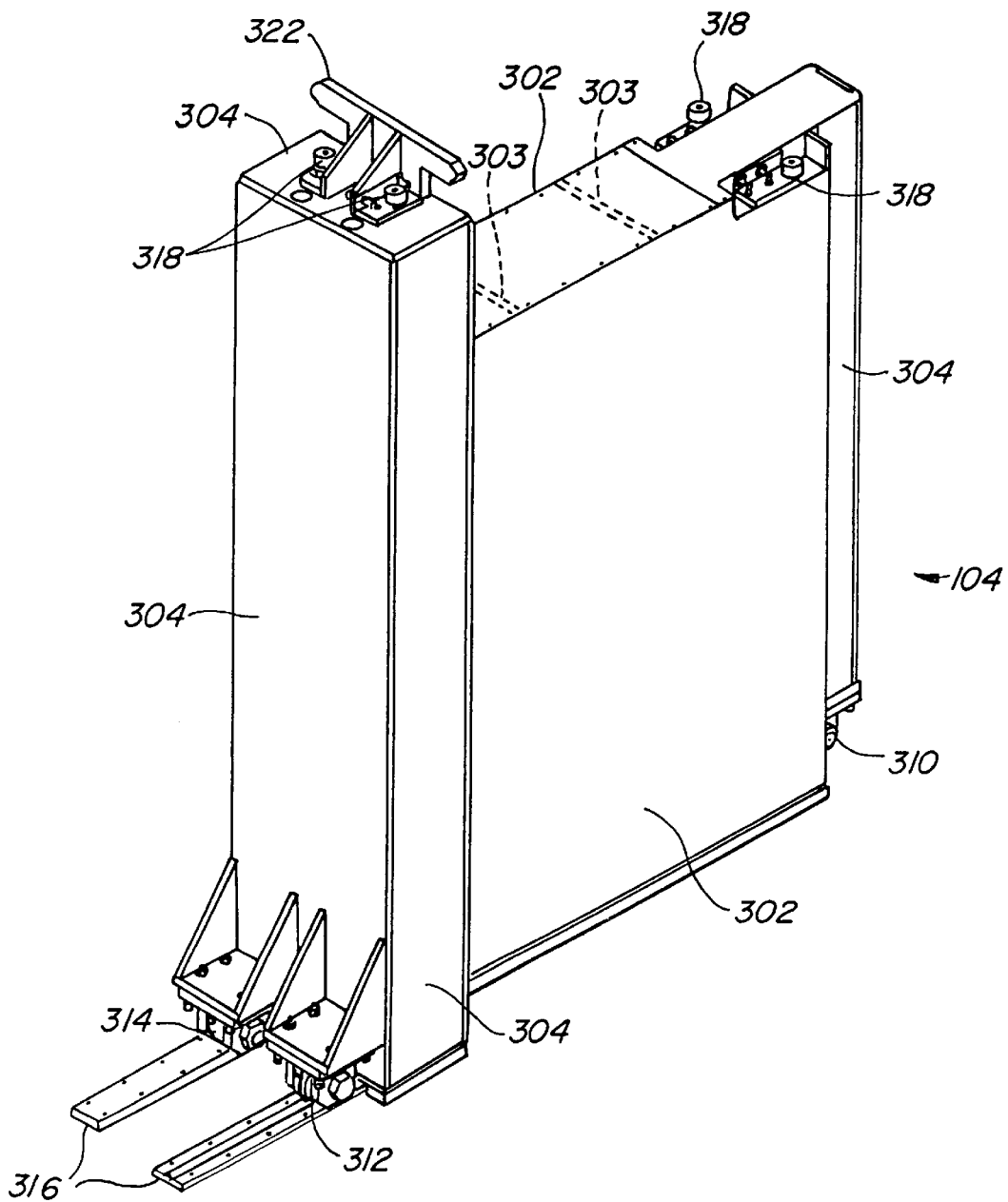
FIG. 3a shows the shielding door in an embodiment of the present invention.

FIG. 3a shows the shielding door 104 in a preferred embodiment of the present invention. The shielding door 104 is placed in one wall of the biological shield 114, as shown in FIG. 1, and provides access for products and operators to the cell area 106. The shielding door 104 incorporates the same fundamental construction as the walls of the biological shield 114 shown in FIG. 2a, including steel plates filled with ballast material. The door structure is fabricated from two three inch steel plates 302 and additional one inch plate sections 304 to complete its unique shape. The shape of the door 104 provides a minimum of three steps at every interface to the biological shield 114. The three steps ensure adequate radiation protection is achieved through Compton Scattering. The use of stepped interfaces for radiation shielding is commonly accepted in the industry. The door 104 also includes two one inch steel stiffener panels 303 between the steel plates 302.

The shielding door 104 is supported on a V-grooved wheel 310 on the front and one V-grooved wheel 312 and one flat profile wheel 314 on the back. The wheels are steel in construction and are rated at 45,000 pounds capacity and supplied by Osborne Ltd. Preferably, the wheels run on hardened steel track 316 fabricated from 8620 steel hardened to 60–65 Rockwell C with a surface flatness within 0.010 inches. The top of the door is supported by RBC #S 96 LW cam followers 318 which support the door vertically.

Figure 3B:
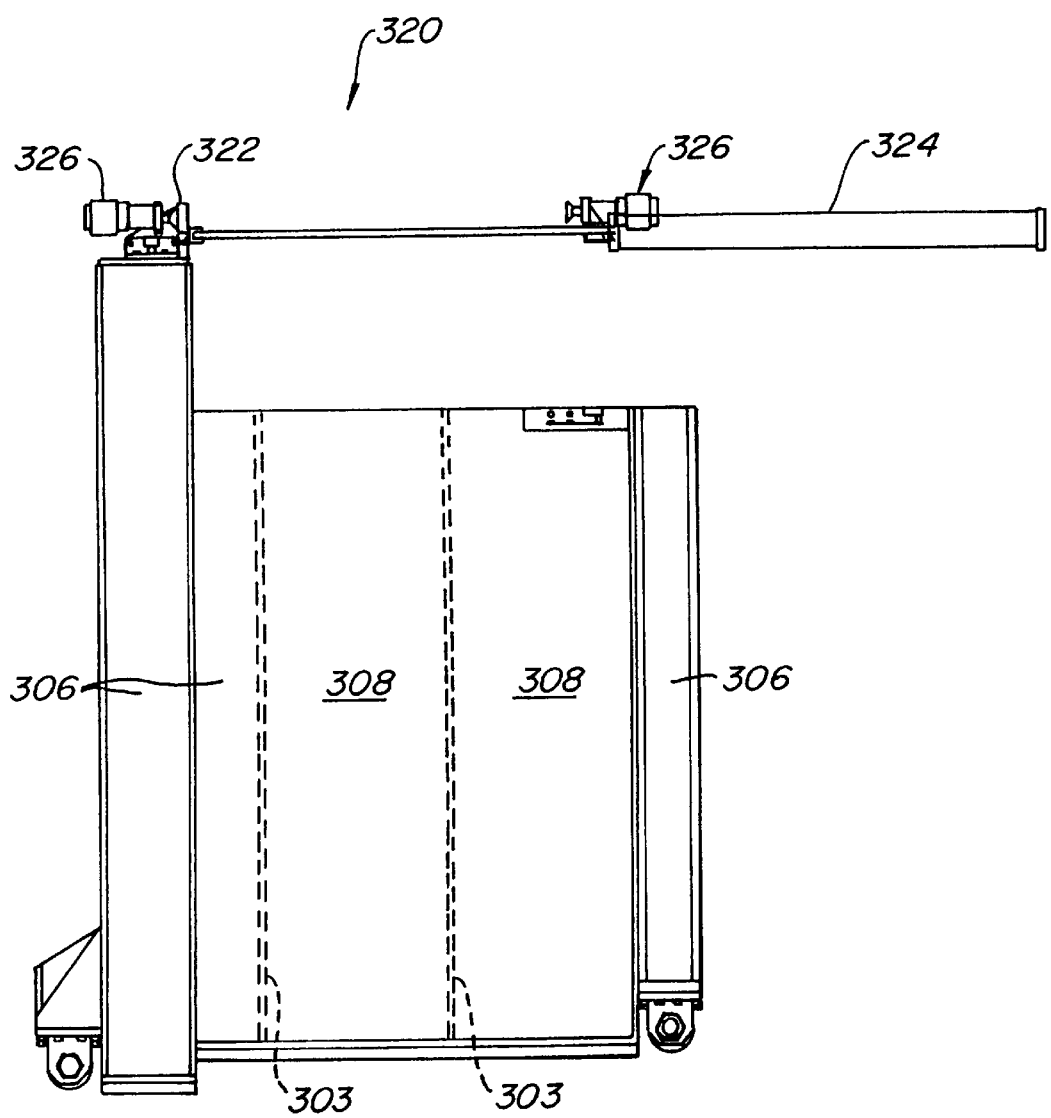
FIG. 3b shows an elevation of the shielding door in an embodiment of the present invention.

FIG. 3b is an elevation of the shielding door 104 shown in FIG. 3a. The fill material for the central compartments of the shielding door 104 is lead shot material 308 preferably with a minimum poured in place density of 435 pounds per cubic foot. The fill material for compartments that are not directly in line with the biological shield 114 opening is the same steel ballast 306 that is used in the biological shield 114. Steel ballast may be used as fill material in all parts of the door. However, the lead shot allows the door threshold to be thinner.

The door movement mechanism 320 is controlled by the control and monitoring system 116 and opens the door when the processing of a batch of material is complete. The mechanism includes a pneumatic cylinder 324 connected to the shielding door 104 at a cylinder mounting plate 322. The shielding door 104 includes hydraulic bumpers 326 to absorb the dynamic load of the door movement. The door movement mechanism 320 is mounted on the shield roof and connected to the shielding door 104 by the cylinder mounting plate 322 to allow for access by the operator in the event there is a failure or maintenance is required, alleviating the need to enter the cell area. This design philosophy inherently improves the safety and reliability of the entire system. In addition the movement of the door is fully connected to the control and monitoring system 116 of the irradiator to ensure the appropriate level of redundancy as defined in USNRC regulations 10 CFR part 36 and American Nation Standards Institute ("ANSI") N43.10 standards.

Material Handling System

Figure 4:
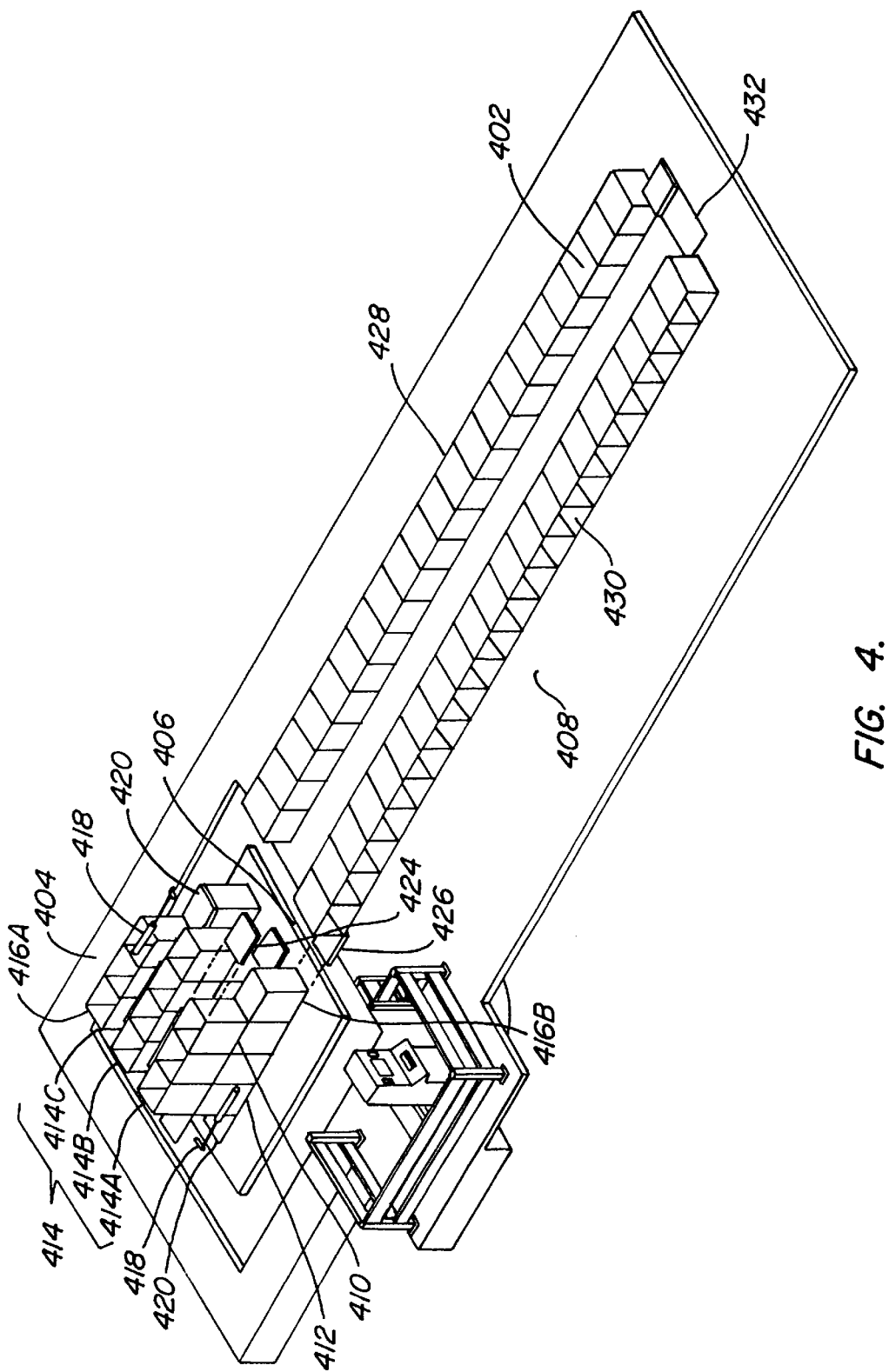
FIG. 4 shows the tote box material handling system in an embodiment of the present invention.

FIG. 4 shows the material handling system 102 in a preferred embodiment of the invention. The material handling system 102 in a preferred embodiment of the present invention is a batch operated tote box system. A series of tote boxes 402 holds the product to be processed. The material handling system 102 functions to move the tote boxes 402 into, around, and out of the cell area 106. It is divided into three components. The internal source pass component 404 located inside the cell area 106, the tote interchange component 406 located near the shielding door 104, and the product loading and unloading component 408 located outside of the cell area 106. The tote boxes 402, once loaded, are moved toward the cell area 106 by the loading and unloading component 408. The tote boxes are transported into the cell area 106 by the tote interchange component 406. The internal source pass component 404 of the material handling system 102 cycles the tote boxes through 21 individual dwell positions. When the cycle is complete, the processed product is removed from the cell area 106 by the tote interchange component 406, and the next batch is loaded by the operator in the loading and unloading component 408.

The internal source pass component 404 is a three pass, two level batch recirculating mechanism. A total of 21 tote boxes 402 comprise a full batch in the cell area 106. The internal source pass component 404 consists of upper 410 and lower 412 level conveyors of a free roller type design on each of three source pass lanes 414A, 414B, and 414C. Additionally, two level changing pneumatic elevators 416A and 416B and several pneumatically driven lane pushers 418 and pass cross transfer mechanisms 420 are used to move the tote boxes 402 around the cell area 106.

The tote boxes enter the cell area 106 through the shielding door 104 on the lower level conveyor 412 on the first source pass lane 414A. As subsequent tote boxes enter the cell area 106, the tote boxes already on the lower level conveyor 412 are pushed forward. Cross transfer mechanisms 420, comprising a pneumatically driven free roller carriage, are positioned to move a tote box 402 to the next source pass lane when it reaches the end of a source pass lane 414A and 414B. The first pneumatic elevator 416a is positioned to move a tote box 402 to the upper level conveyor 410 when it reaches the end of the third source pass lane 414C on the lower level conveyor 412. The tote box 402 moves in a similar but reverse manner through the upper level conveyor 410 for each of the three source pass lanes 414C, 414B, and 414A. The second pneumatic elevator 416B is positioned to lower a tote box 402 to the lower level conveyor 412 when the tote box 402 reaches the end of the first source pass lane 414A and the irradiator is in the processing mode. The lane pushers 420 are positioned to index tote boxes 402 forward, one position at a time in a shuffle and dwell manner.

The tote interchange component 406 removes the tote boxes 402 containing processed product from the cell area 106 during the interchange mode while simultaneously placing tote boxes with unprocessed product in the cell area 106 for the next batch operation. The interchange component 406 is made up of several pneumatically driven devices which are designed to bridge the gap across the shielding door 104 and remove or deliver tote boxes 402 between the loading and unloading component 408 and the internal source pass component 404. During interchange mode, the second pneumatic elevator 416B of the internal source pass component 404 does not deliver tote boxes 402 to the lower level conveyor 412. Instead, a first pneumatically driven free roller carriage 424 of the interchange component 406 is positioned near the second pneumatic elevator 416B to allow the last tote box 402 on the first source pass lane 414A on the upper level conveyor 410 to be pushed out of the cell area 106 onto the first pneumatically driven free roller carriage 424 when the lane pusher moves the tote boxes 402 on the internal source pass component 404 one position. The first pneumatically driven free roller carriage 424 is constructed to be able to move back and forth across the shielding door 104 threshold to the area outside of the cell area 106.

A second pneumatically driven free roller carriage 426 carrying a tote box 402 with unprocessed product is positioned to simultaneously move across the threshold of the shielding door 104 into position at the end of lane 414A of the lower level conveyor 412. A lane pusher 418 is positioned to push the tote box 402 from the second pneumatically driven free roller carriage 426 onto the lower level conveyor 412. The second pneumatically driven free roller carriage 426 is constructed to be able to move back and forth across the threshold of the shielding door 104 and outside of the cell area 106.

Figure 5:
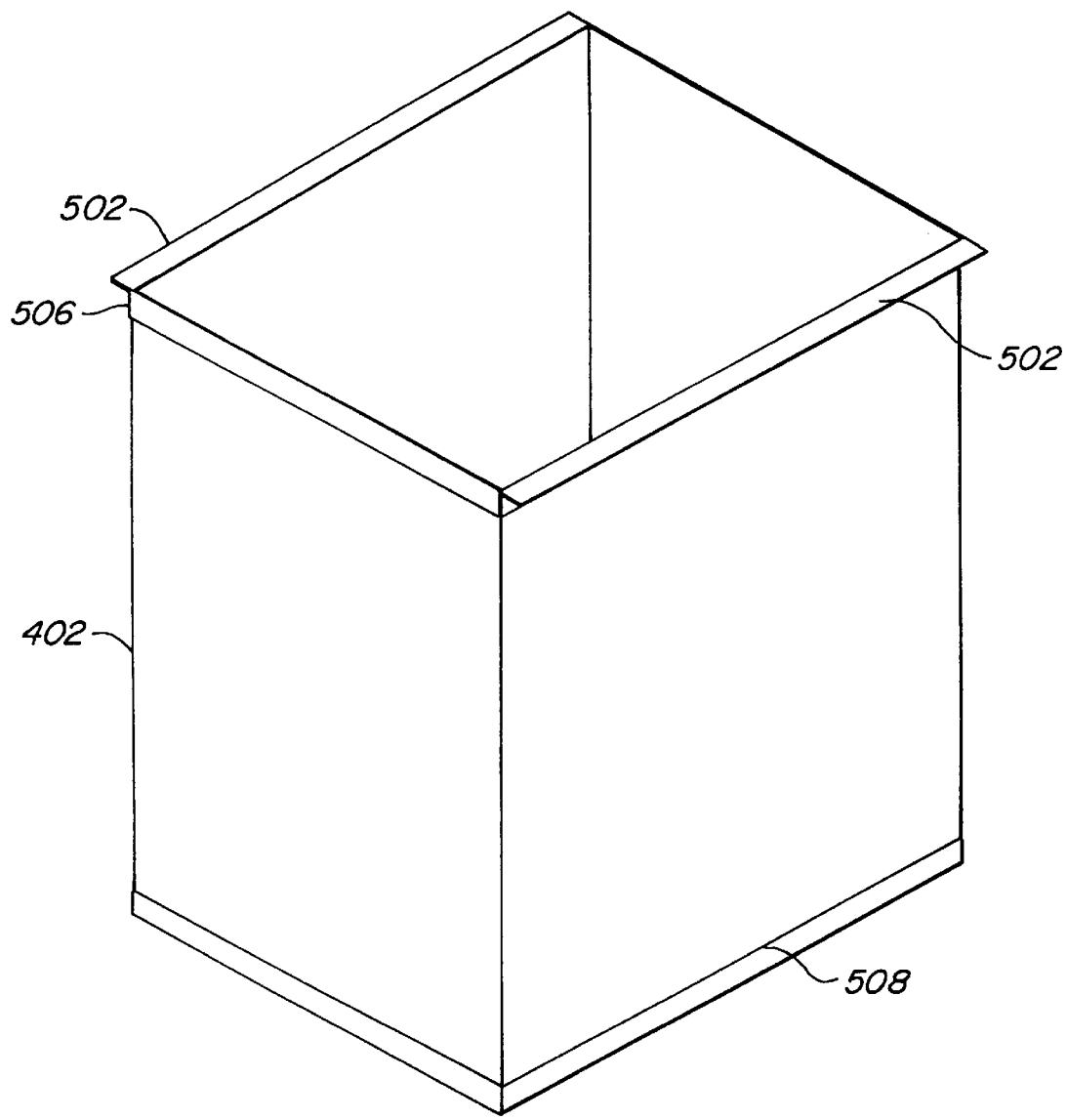
FIG. 5 shows the product tote box used in an embodiment of the present invention.

The loading and unloading component 408 consists of two lanes of conveyor 428 and 430. The first lane of conveyor 428 carries the tote boxes 402 which contain the product to be processed to the interchange component 406 for loading into the cell area 106. The second lane of conveyor 430 carries the tote boxes 402 which contain the processed product from the interchange component 406 into position for manual unloading. A pneumatically driven free roller cross transfer carriage 432 is positioned at the end of the two lanes 428 and 430. This cross transfer carriage can move tote boxes 402 from one lane to the other. The two lanes 428 and 430 have the capability of being tilted through any angle up to 90 degrees by a "Eurodrive" driven shaft mechanism. Tilting the tote boxes 402 enables the operators to easily load or unload product from the tote boxes 402. When the next batch scheduled for processing has been loaded and the previous batch unloaded, the tote boxes 402 are rotated back to vertical and wait for the next interchange cycle, The tote box 402 in a preferred embodiment of the present invention is shown in FIG. 5. The tote box 402 is made of stainless steel sheet. In an irradiator with a biological shield 114 of the size mentioned above, the tote box 402 preferably will have inside dimensions of 24 inches wide by 30 inches long by 36 inches high and a wall thickness of 0.037 inches. This size optimizes the tote box to source overlap. Other dimensions could have been chosen within the same invention. Preferably, the width may vary from 16 to 30 inches, the length from 20 to 40 inches, and the height from 24 to 40 inches. If a larger tote box 402 is chosen, the internal dimensions of the biological shield 114 may need to be increased to fit the increased size of the mechanism inside the biological shield 114. The tote box 402 has two one inch stainless steel structural angles 502, welded to a top edge of the tote box 402 to support it in the upper level conveyor 410 in the cell area 106. This design insures that there is minimal material between the two source pass levels and provides less attenuation for the gamma radiation to the product. The bottom of the tote box 402 is a stainless steel pan 508 which supports the product inside. Both the bottom and the top of the tote box 402 have $\frac{1}{8}$ inch stainless steel stiffener bars 506 welded to the tote box. The overall weight capacity of a 15 cubic foot tote box is 450 pounds.

Source System

The source system 112 provides a location in which the radiation source, preferably cobalt-60 capsules, are stored, a mechanism to move the radiation source into and out of the cell area 106, and a mechanism to load and unload the cobalt-60 capsules from two source racks 110 during source interchange procedures. For convenience, in FIGS. 6 and 7 one source rack 110 is shown. Both source systems preferably include a second source rack 110 directly behind and parallel to the source rack shown in FIGS. 6 and 7. Wet or dry type source systems can be used in the present invention. The type of storage used will depend upon the ground conditions for excavation and the specific regulatory environment in the geographic area of the site. Usually, in cases where there are no physical or regulatory barriers, the industry standard wet storage design will be used.

Figure 6:
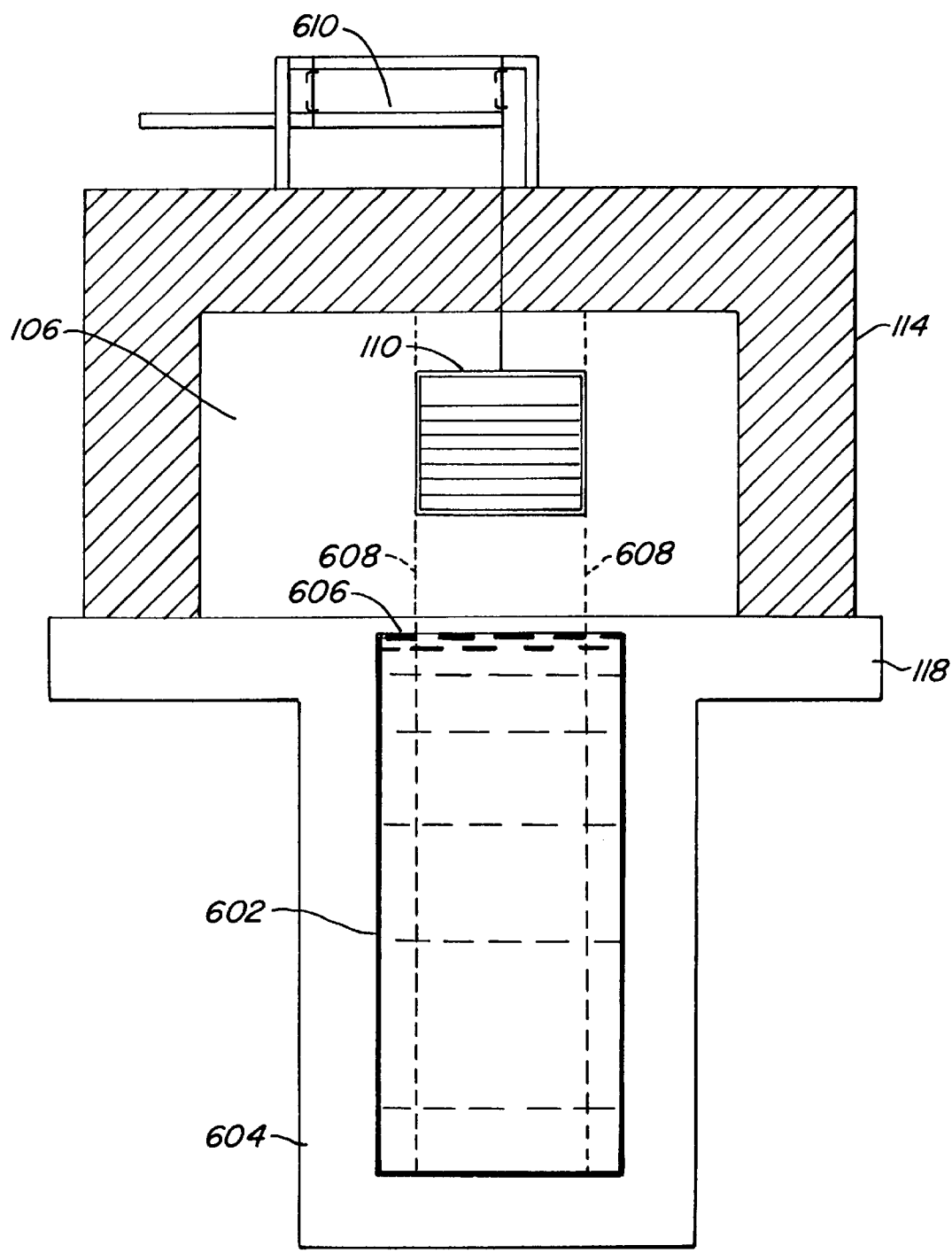
FIG. 6 shows an elevation of the wet type source system in an embodiment of the present invention.

FIG. 6 shows a preferred embodiment of a wet type source system 112. The wet type source system 112 stores radiation sources in a pool of deionized water 606. The pool of deionized water 606 guards against radiation exposure during normal operations, when moving the capsules into and out of the source racks 110, and when loading and unloading new radiation source. The pool of deionized water 606 is shaped to handle a shipping container containing new radiation source for loading into the source racks 110.

The wet type source system 112 in an embodiment of the present invention has a steel cylindrical pool liner 602. The pool liner 602 is made of type 304 stainless steel preferably with an inside diameter of seven feet. The depth of the pool liner 602 is preferably 16 feet from the cell area 106 floor level. The cylindrical design of the pool allows both stronger structural strength than the standard rectangle or "L" shaped pools commonly used in the industry. The cylindrical shape also allows the use of drilling type excavation techniques to insert the pool liner 602 into the system foundation 118. The drilling excavation will be much less disruptive than for other types of source systems to any operation in the area and therefore is more appropriate for installations in existing buildings where space permits the drilling rig to work. All construction on the pool liner 602 must be done by certified welders and all welds must be leak checked using an industry standard method such as dye penetrant testing. Both of these manufacturing details are industry standard.

The pool liner 602 is inserted into an excavation 604 prior to the assembly of the biological shield 114. The system foundation 118 is poured around the pool liner 602. The pool liner 602 holds the pool of deionized water 606 which is continuously recirculated to maintain the industry required 20 microsiemens/cm conductivity to prevent corrosion of source capsules supplied by the radiation source manufacturer. The water treatment systems utilized on this design are standard industrial deionization and chilling systems using a closed loop water flow design in accordance with industry requirements.

The wet type source system 112 includes a mechanism for handling the source capsules for reloading, which is common in the irradiation industry. A pneumatically driven source rack hoist system 610 is mounted on the roof of the biological shield 114 and includes a double valve redundant interlock design for each of the two hoists to ensure both safe operation for lifting and redundancy in returning the source racks 110 to the pool of deionized water 606. The source racks 110 are attached to the source rack hoist system. They are positively guided through their travel by taut stainless steel cables 608.

A second option for the source system 1 12 in the present invention is a dry type source system. The dry type source system 112 option is shown in FIG. 7. In the dry type source system 112, the storage area is a six feet deep steel sheet and lead brick shielded and type 304 stainless steel lined pit 702 below the floor of the cell area 106. A triple stepped, lead shot filled, steel encased plug 704 is attached to the top of the source racks 110 and covers the pit opening when the source racks are in the pit 702. The plug 704 prevents radiation from leaving the pit 702. A combination of two, in floor, eight inch diameter ducts 706 provides 2000 SCFM of air ventilation past the source racks 110 to ensure the source, in the stored position, remains below the radiation source suppliers published temperature limits. The ducts are positioned to deliver air to the pit horizontally across the major areas of both source racks 110 to provide adequate convection type cooling. This design is achieved using a series of 1 inch diameter nozzles 708 at the inlet side of the ventilation and a full height exhaust grill 710 on the outlet.

The dry type source system requires a shallower excavation than the wet type source system. If the area in which the irradiator is to be installed has deep excavation problems such as troublesome soil conditions or a high water level, the dry option may be selected.

The dry type source system 112 includes one hoist 716 for each of two identical parallel source racks 110 which lift the stepped plug 704 along with the source racks 110 out of the pit 702 into the operating position. The plug 704 and source racks 110 are guided by 1 inch diameter stainless steel rods 718 which ensure that the assembly does not rotate inside the cell area 102 as well as provide positive guidance into and out of the pit 702.

The dry type source system 112 also includes a lead glass window 712, which shields the energy from two Megacuries of cobalt-60, and two "Ball and Tong" type manipulators 714, which are used to physically handle the source capsules inside the room. These components allow a trained operator to see and physically handle the source inside the cell area 106 during loading of new source capsules. Once all new capsules have been loaded, the cell area 106 is returned to its operating state, the window 712 and manipulators 714 are removed and stored for another loading.

The source capsules utilized in this design are the industry standard doubly encapsulated sealed source approximately 18 inches long by ⅜ of an inch in diameter.

Control and Monitoring System

The control and monitoring system 116 in a preferred embodiment of the present invention is controlled by a programmable logic controller (PLC) and uses a Supervisory control and data acquisition system (SCADA) for monitoring both the operating and safety functions of the irradiator. PLC/SCADA packages are commercially available which meet both the design and regulatory requirements for this type of irradiator system.

Method

The method of the invention safely and economically irradiates products by subjecting them to predetermined amounts of gamma radiation. The use of the apparatus described above will now be set forth in more detail.

After the radiation source is loaded into the irradiator using a hoist system that is well known in the art, the source, which is supplied by a licensed manufacturer of sealed sources in standard size capsules, is then loaded into the source racks 110. If the irradiator uses a wet storage system as shown in FIG. 6, the method for loading the source capsules is standard in the industry. The source capsules are loaded while they are in the storage pool 602, and the operator observes them directly through the water 606. If the irradiator uses a dry storage system as shown in FIG. 7, the operator must remotely handle the source capsules from outside of the biological shield 114. As shown in FIG. 7, the operator uses a lead glass window 712 which shields the radiation energy. The operator uses two ball and tong type manipulators 714 to load the source capsules into the source racks 110 while the source racks 1O are out of the storage pit 702. The source capsules remain in the source system 112 for their useful life.

After the source is loaded into the source system 112, the product to be processed is loaded into the cell area 106 by using the material handling system 102. As shown in FIG. 4, and operator physically loads the empty tote boxes 402 in the first lane of conveyor 428 in the loading and unloading component 408 with product to be processed. After the tote boxes 402 are loaded, the operator tilts the tote boxes to a vertical position. The control and monitoring system 116 automatically switches the irradiator to interchange mode after the batch of product in the cell area 106 is processed. The tote boxes 402 are transported into the cell area 106 by the material handling system 102. As the new product is being transported into the cell area 106, processed product is exiting the cell area 106 onto the second lane of conveyor 430 into a position for unloading. The tote boxes 402 may be tilted to ease removal of the processed product form the tote boxes 402.

When each of the 21 positions of the internal source pass component 404 is filled with a tote box 402 of unprocessed product, the irradiator is put into processing mode at the control and monitoring system 116 by the operator. The control and monitoring system 116 automatically closes the shielding door 104 and, after the operator confirms the processing time at the control and monitoring system 116, lifts the source racks 110 either out of the pool 606, if the irradiator has a wet source system, or out of the pit 702, if the irradiator has a dry source system into the cell area 106. The internal source pass component 404 then cycles the tote boxes 402 through 21 individual dwell positions on the three pass, two level configuration shown on FIG. 4 and described above. When the cycle is complete, the source racks 110 are lowered into the pool 606 or pit 702, the shielding door 104 is opened and the material handling system 102 automatically switches into the interchange mode of operation. The processed product is automatically transported out of the cell area 106, and then manually unloaded from the tote boxes 402 on the loading and unloading component 408 of the material handling system 102.

If the cell needs to be physically entered at any time, the control and monitoring system 116 will force the operator to fully reset all cell area lock out procedures as specified in ANSI N43.10.

While the present invention has been described in connection with certain preferred embodiments, many other embodiments will be apparent to those skilled in the art based on the present disclosure. The present invention is not limited to the embodiments described in the disclosure. Rather, the scope of the invention is defined by the claims.

What is claimed is:

1. An apparatus for irradiating products, comprising:
    a cell area;
    a biological shield surrounding the cell area, including a roof, wherein said biological shield is constructed of removable modules;
    a shielding door in the biological shield shaped to achieve at least three radiation scatters at each contact with the biological shield;
    two radiation source racks inside of the cell area; and
    a material handling conveyor system which delivers the products, via the shielding door, into and out of the cell area where the products are irradiated.
2. The apparatus of claim 1, wherein the modular walls of the biological shield have an outer panel and an inner panel, and ballast material between the outer panel and the inner panel.
3. The apparatus of claim 2 wherein the outer panel and the inner panel are metal.
4. The apparatus of claim 3, wherein the modules further comprise metal stiffeners perpendicular to and attached to the outer steel panel and the inner steel panel.
5. The apparatus of claim 3 wherein the metal is steel.
6. The apparatus of claim 5 wherein the steel panels are at least about one-half inch thick.
7. The apparatus of claim 6 wherein the ballast material is steel shot.
8. The apparatus of claim 7 wherein the steel ballast is at least about 36 inches thick.
9. The apparatus of claim 3, wherein the
    shielding door has an outer metal panel, an inner metal panel, and ballast material between the outer metal panel and the inner metal panel.
10. The apparatus of claim 9, wherein the material handling system is a batch operated system.
11. The apparatus of claim 10, wherein the material handling system comprises
    a series of tote boxes;
    a pneumatically driven conveyor system which circulates the tote boxes around a radiation source holder; and
    a series of pneumatically driven elevators and carriages which deliver the tote boxes into the cell area and remove the totes after processing.
12. The apparatus of claim 11, further comprising a pneumatically driven conveyor system for unloading and loading the tote boxes which
    tilts the tote boxes up to 90° from vertical and
    is constructed to allow simultaneous loading and unloading of the tote boxes.
13. The apparatus of claim 11, wherein
    the pneumatically driven conveyor system has an upper and a lower level;
    the radiation source holder comprises a first source rack and a second source rack;
    the tote boxes are conveyed sequentially past an outer surface of the first source rack, between an inner surface of the first source rack and an inner surface of the second source rack, and past an outer surface of the second source rack on the lower level;
    the tote boxes are conveyed sequentially past the outer surface of the second source rack, between the inner surface of the first source rack and the inner surface of the second source rack, and past the outer surface of the first source rack on the upper level; and
    a first pneumatically driven elevator delivers the tote boxes from the upper level to the lower level and a second pneumatically driven elevator delivers the tote boxes from the lower level to the upper level.
14. The apparatus of claim 2 wherein the outer panel and the inner panel are reinforced concrete.
15. The apparatus of claim 14 wherein the inner concrete panel is at least about 8 inches thick, the outer concrete panel is at least about 8 inches thick, and the inner roof is at least about 12 inches thick.
16. The apparatus of claim 15 wherein the ballast material is steel shot.
17. The apparatus of claim 16 wherein the steel ballast is at least about 28 inches thick.
18. A method of subjecting material to radiation, comprising the steps of:
    providing a source of radiation in a cell area;
    providing a biological shield of modular construction, including a roof and a shielding door shaped to achieve at least three radiation scatters at each contact with the biological shield, surrounding the cell area;
    automatically transporting the material by conveyor through the shielding door into the cell area;
    closing the shielding door; and
    subjecting the material to radiation from the radiation source.
19. The method as claimed in claim 18, wherein the dosage of radiation from the radiation source is sufficient to sanitize or sterilize the material.

* * * * *